US006794328B2

United States Patent
Yokozawa et al.

(10) Patent No.: US 6,794,328 B2
(45) Date of Patent: Sep. 21, 2004

(54) DIPHOSPHINE COMPOUND, PRODUCTION INTERMEDIATE THEREOF, TRANSITION METAL COMPLEX CONTAINING THE COMPOUND AS LIGAND AND ASYMMETRIC HYDROGENATION CATALYST CONTAINING THE COMPLEX

(75) Inventors: Tohru Yokozawa, Hiratsuka (JP); Takao Saito, Hiratsuka (JP)

(73) Assignee: Takasago International Corporation, Tokyo (JP)

(*) Notice: Subject to any disclaimer, the term of this patent is extended or adjusted under 35 U.S.C. 154(b) by 0 days.

(21) Appl. No.: 10/452,729

(22) Filed: Jun. 3, 2003

(65) Prior Publication Data
US 2003/0228977 A1 Dec. 11, 2003

(30) Foreign Application Priority Data
Jun. 4, 2002 (JP) .................................... P. 2002-162463

(51) Int. Cl.$^7$ .............................. B01J 31/00; C07F 9/50
(52) U.S. Cl. ....................... 502/162; 502/166; 549/206; 549/208; 549/216
(58) Field of Search ................................ 502/162, 166; 549/200, 206, 208, 162, 166

(56) References Cited

U.S. PATENT DOCUMENTS

| | | | |
|---|---|---|---|
| 4,604,474 A | | 8/1986 | Kumobayashi et al. |
| 4,691,037 A | | 9/1987 | Yoshikawa et al. |
| 5,223,632 A | | 6/1993 | Ishizaki et al. |
| 5,326,801 A | * | 7/1994 | Foa et al. .................... 524/109 |
| 6,248,848 B1 | * | 6/2001 | Tamao et al. ................ 526/274 |
| 6,333,291 B1 | * | 12/2001 | Yokozawa et al. .......... 502/162 |
| 6,333,435 B1 | * | 12/2001 | Cai et al. ...................... 568/17 |
| 6,566,298 B2 | * | 5/2003 | Driessen-Holscher et al. ... 502/166 |

FOREIGN PATENT DOCUMENTS

| | | |
|---|---|---|
| EP | 1 095 946 A1 | 5/2001 |
| JP | 55-61937 A | 5/1980 |
| WO | WO 01/21625 A1 | 3/2001 |

OTHER PUBLICATIONS

CA:133:177291 abs of Tetrahedron: Asymmetry by Che et al, 11(9) pp 1919–1925 2000.*

J. Chem. Soc., Chem. Commun., 1985, 922–924.

J. Chem. Soc., Chem. Commun., 1989, 1208–1210.

J. Am. Chem. Soc. 1991, 113, 9887–9888.

Rudolf Schmid et al., "102, Axially Dissymmetric Bis(triaryl) phosphines in the Biphenyl Series: Synthesis of (6.6–Dimethylbiphenyl–2,2–diyl)bis(diphenylphosphine) ('BIPHEMP') and Analogues, and their Use in Rh(I)–Catalyzed Asymmetric Isomerizations of N,N–Diethylnerylamine", (1998), Helvetica Chimica ACTA, vol. 71, No. 4, pp. 897–929.

* cited by examiner

*Primary Examiner*—Jean F. Vollano
(74) *Attorney, Agent, or Firm*—Sughrue Mion, PLLC

(57) ABSTRACT

The present invention provides a novel phosphine compound, specifically to provide a novel phosphine compound useful as a ligand for the above catalysts, in particular, a novel catalyst having an excellent performance (chemical selectivity, enantio-selectivity, catalytic activity) as a catalyst for asymmetric synthetic reactions, particularly asymmetric hydrogenation. A diphosphine compound represented by the general formula (1):

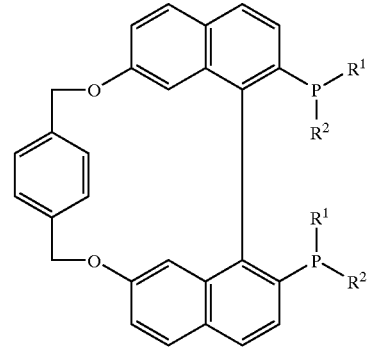

(1)

wherein $R^1$ and $R^2$ each independently represents a lower alkyl group, a cycloalkyl group, an unsubstituted or substituted phenyl group, or a five-membered heteroaromatic ring residue.

7 Claims, No Drawings

DIPHOSPHINE COMPOUND, PRODUCTION INTERMEDIATE THEREOF, TRANSITION METAL COMPLEX CONTAINING THE COMPOUND AS LIGAND AND ASYMMETRIC HYDROGENATION CATALYST CONTAINING THE COMPLEX

FIELD OF THE INVENTION

The present invention relates to a novel diphosphine compound, a production intermediate thereof, a transition metal complex containing the diphosphine compound as a ligand, and a transition metal complex catalyst useful as a catalyst for various asymmetric syntheses.

BACKGROUND OF THE INVENTION

Hitherto, many reports have been made on transition metal complexes capable of being utilized in asymmetric syntheses such as asymmetric hydrogenation, asymmetric isomerization, and asymmetric hydrosilylation. Particularly, a complex where an optically active tertiary phosphine coordinates to a transition metal such as ruthenium, rhodium, iridium, or palladium exhibits excellent performance as a catalyst for asymmetric synthetic reactions.

In order to further enhance the performance, a large number of phosphine compounds having various structures have been hitherto developed (The Chemical Society of Japan ed., Kagaku Sosetsu (Chemical Review) 32 Yuki Kinzoku Sakutai no Kagaku (Chemistry of Organic Metal Complexes), pp. 237–238, 1982; *Asymmetric Catalysts In Organic Synthesis*, written by Ryoji Noyori, A Wiley-Interscience Publication). In particular, 2,2'-bis (diphenylphosphino)-1,1'-binaphthyl (hereinafter referred to as "BINAP") is one of excellent optically active phosphines, and there have been already reported a rhodium complex (JP-A-55-61937) and a ruthenium complex (JP-B-4-81596 corresponding to U.S. Pat. No. 4,691,037) containing the BINAP as a ligand. Moreover, it has been also reported that a rhodium complex (JP-B-1-42959 corresponding to U.S. Pat. No. 4,604,474) and a ruthenium complex (JP-B-4-81596 corresponding to U.S. Pat. No. 4,691,037) containing 2,2'-bis(di-(p-tolyl)phosphino)-1,1'-binaphthyl (hereinafter referred to as "p-TolBINAP") as a ligand affords good results in asymmetric hydrogenation and asymmetric isomerization. Furthermore, JP-B-7-68260 corresponding to U.S. Pat. No. 5,223,632 reports that a ruthenium complex of 2,2'-bis(di-(3,5-dialkylphenyl)phosphino)-1,1'-binaphthyl affords excellent results in asymmetric hydrogenation of β-ketoesters.

However, since selectivity (chemical selectivity, enantio-selectivity) and catalytic activity are not always satisfactory depending on objective reaction or its reaction substrate, improvement of the catalysts are sometimes required.

SUMMARY OF THE INVENTION

It is an object of the invention to provide a novel phosphine compound and specifically, it is an object to provide a novel phosphine compound useful as a ligand for the above catalysts. Moreover, it is another object to provide a novel catalyst having an excellent performance (chemical selectivity, enantio-selectivity, catalytic activity) as a catalyst for asymmetric synthetic reactions, particularly asymmetric hydrogenation.

As a result of extensive studies for solving the above problems, the present inventors have found that a transition metal complex containing an optically active isomer of a diphosphine compound having a specific structure as a ligand is effective as a catalyst component which participates in asymmetric hydrogenation. In addition, they have found that the transition metal complex exhibits excellent catalytic activity and enantio-selectivity in asymmetric hydrogenation. Based on the findings and further investigation, they have accomplished the invention.

Thus, the present invention provides:

(i) A diphosphine compound represented by the general formula (1):

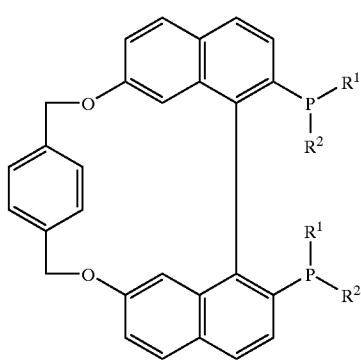

(1)

wherein $R^1$ and $R^2$ each independently represents a lower alkyl group, a cycloalkyl group, an unsubstituted or substituted phenyl group, or a five-membered heteroaromatic ring residue.

(ii) A compound represented by the general formula (2):

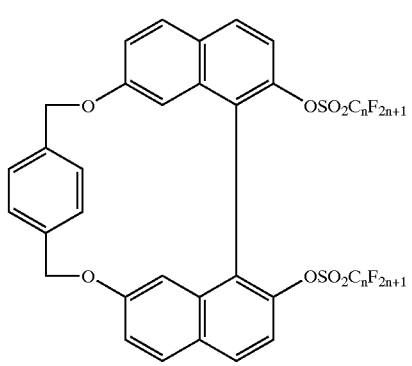

(2)

wherein n is an integer of 1 to 3.

(iii) A compound represented by the general formula (3):

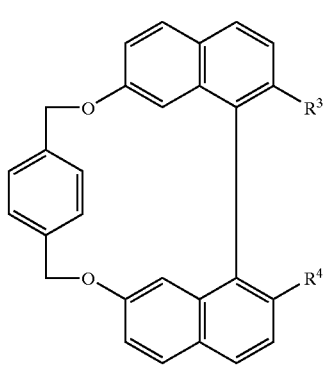

(3)

wherein $R^3$ and $R^4$ each independently represents a hydroxy group, a protected hydroxy group, a lower alkoxy group, a chlorine atom, or a bromine atom.

(iv) A transition metal complex containing an optically active compound of the compound according to (i) above and a transition metal selected from the group consisting of rhodium, ruthenium, iridium, palladium, and nickel.

(v) A catalyst containing a transition metal complex represented by the general formula (4):

$$M_mL_nX_pQ_q \quad (4)$$

wherein M is a transition metal selected from rhodium, ruthenium, iridium, palladium, and nickel and L represents an optically active diphosphine compound of the compound according to (i) above; X is selected from the group consisting of Cl, Br, I, an acetoxy group, a methallyl group, and a π-allyl group; and Q is selected from the group consisting of $NEt_3$ (wherein Et represents an ethyl group) and an dialkylammonium ion,
provided that when M=Rh, X=Cl, Br, or I and m=2, n=2, p=2, and q=0, when M=Ru and X=an acetoxy group, m=1, n=1, p=2 and q=0, when M=Ru and X=a methallyl group, m=1, n=1, p=2 and q=0, when M=Ru, X=Cl, Br, or I, and Q=$NEt_3$, m=2, n=2, p=4, and q=1, when M=Ru, X=Cl, Br, or I, and Q=an dialkylammonium ion, m=n=2, p=5, and q=1, when M=Ir, X=Cl, Br, or I and m=2, n=2, p=2, and q=0, when M=Pd and X=Cl, Br, or I, m=1, n=1, p=2, and q=0, when M=Pd and X=a π-allyl group, m=2, n=2, p=2, and q=0, and when M=Ni, X=Cl, Br, or I and m=1, n=1, p=2, and q=0.

(vi) A catalyst containing a transition metal complex represented by the general formula (5):

$$[M_mL_nX_pZ_q]Y_r \quad (5)$$

wherein M is a transition metal selected from rhodium, ruthenium, iridium, palladium, and nickel and L represents an optically active diphosphine compound of the compound according to (i) above; X is selected from the group consisting of a π-allyl group, cod, nbd, Cl, Br, and I; Z represents benzene or p-cymene; and Y is selected from the group consisting of $BF_4$, $ClO_4$, $PF_6$, $BPh_4$, Cl, Br, and I, and cod represents 1,5-cyclooctadiene, nbd represents norbornadiene, and Ph represents a phenyl group, provided that when M=Rh, X=cod or nbd, Y=$BF_4$, $ClO_4$, $PF_6$, or $BPh_4$, and m=1, n=1, p=1, q=0, and r=1, when M=Ru and Y=Cl, Br, or I, X=Cl, Br, or I, Z=benzene or p-cymene, and m=1, n=1, p=1, q=1, and r=1, when M=Ru and Y=$BF_4$, $ClO_4$, $PF_6$, or $BPh_4$, m=1, n=1, p=0, q=0, and r=2, when M=Ir, X=cod or nbd, Y=$BF_4$, $ClO_4$, $PF_6$, or $BPh_4$, and m=1, n=1, p=1, q=0, and r=1, when M=Pd and X=a π-allyl group, Y=Cl, Br, I, $BF_4$, $ClO_4$, $PF_6$, or $BPh_4$ and m=1, n=1, p=1, q=0, and r=1, when M=Pd and p=0, Y=$BF_4$, $ClO_4$, $PF_6$, or $BPh_4$ and m=1, n=1, q=0, and r=1, and when M=Ni, X=Cl, Br, or I and m=1, n=1, p=2, q=0, and r=0.

(vii) A catalyst for asymmetric hydrogenation, which contains the transition metal complex according to (iv) above.

DETAILED DESCRIPTION OF THE INVENTION

The following will explain the invention in detail.

The diphosphine compound of the invention is a compound represented by the following general formula (1):

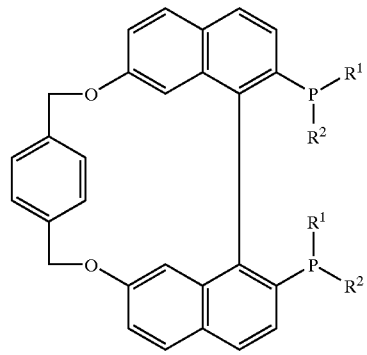

(1)

wherein $R^1$ and $R^2$ each independently represents a lower alkyl group, a cycloalkyl group, an unsubstituted or substituted phenyl group, or a five-membered heteroaromatic ring residue.

The lower alkyl group for the above $R^1$ and $R^2$ is an alkyl group having 1 to 5 carbon atoms, which includes a methyl group, an ethyl group, an n-propyl group, an iso-propyl group, an n-butyl group, an iso-butyl group, a sec-butyl group, a tert-butyl group, an n-pentyl group, an iso-pentyl group, and a neopentyl group. Examples of the cycloalkyl group include cyclopentyl group, cyclohexyl group, and cycloheptyl group.

The substituted phenyl group has from 1 to 5 substituents, preferably from 1 to 3 substituents. The substituent for the substituted phenyl group is preferably an alkyl group having 1 to 5 carbon atoms, an alkoxy group having 1 to 5 carbon atoms, a di(lower alkyl)amino group, or a halogen atom. The alkyl group having 1 to 5 carbon atoms herein includes a methyl group, an ethyl group, an n-propyl group, an iso-propyl group, an n-butyl group, an iso-butyl group, a sec-butyl group, a tert-butyl group, an n-pentyl group, an iso-pentyl group, and a neopentyl group. The alkoxy group having 1 to 5 carbon atoms includes a methoxy group, an ethoxy group, an n-propoxy group, an iso-propoxy group, a tert-butoxy group, and a pentyloxy group. The lower alkyl group for the di(lower alkyl)amino group is an alkyl group having 1 to 5 carbon atoms include a methyl group, an ethyl group, an n-propyl group, an iso-propyl group, an n-butyl group, an iso-butyl group, a sec-butyl group, a tert-butyl group, an n-pentyl group, an iso-pentyl group, and a neopentyl group.

The halogen atom includes a fluorine atom, a chlorine atom, a bromine atom, and iodine atom.

The five-membered heteroaromatic residue is preferably a 2-furyl group, a 3-furyl group, a 2-benzofuryl group, or a 3-benzofuryl group.

Among these compounds, a preferred compound is a compound represented by the general formula (6):

(6)

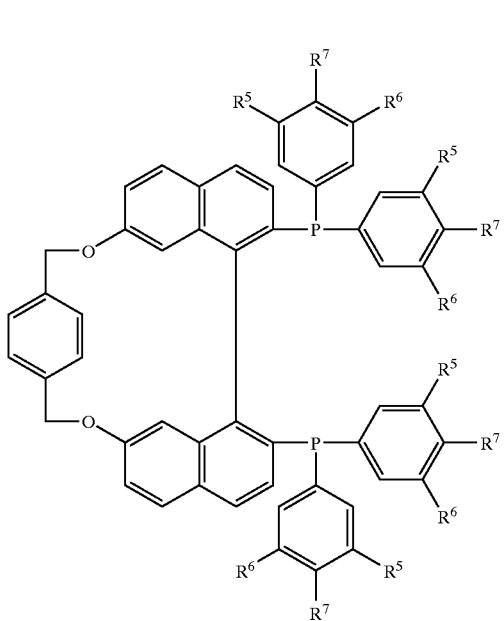

wherein $R^5$ and $R^6$ each independently represents a hydrogen atom, an alkyl group having 1 to 5 carbon atoms, or an alkoxy group having 1 to 5 carbon atoms, and $R^7$ represents a hydrogen atom, an alkyl group having 1 to 5 carbon atoms, an alkoxy group having 1 to 5 carbon atoms, or a di(lower alkyl)amino group. The lower alkyl group herein is an alkyl group having 1 to 5 carbon atoms. In this connection, the alkyl group having 1 to 5 carbon atoms and an alkoxy group having 1 to 5 carbon atoms are functional groups the same as those exemplified in the above.

Among the compounds represented by the above general formula (6), more preferred compounds are those wherein $R^5$ and $R^6$ are the same and are selected from a hydrogen atom, a methyl group, an ethyl group, an n-propyl group, an iso-propyl group, an n-butyl group, and a tert-butyl group and $R^7$ is selected from a hydrogen atom, a methoxy group, an ethoxy group, an iso-propoxy group, and a tert-butoxy group.

The compound represented by the general formula (2) is also a compound belonging to the invention.

(2)

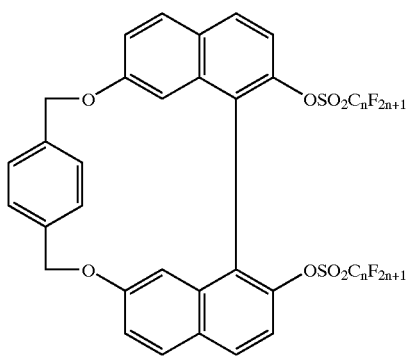

wherein n is an integer of 1 to 3.

The compound represented by the above general formula (2) is a production intermediate for the diphosphine compounds represented by the general formulae (1) and (6).

Furthermore, the compound represented by the general formula (3) is also a compound belonging to the invention.

(3)

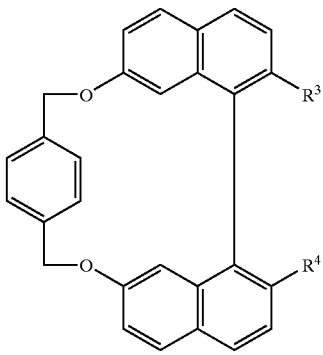

wherein $R^3$ and $R^4$ each independently represents a hydroxy group, a protected hydroxy group, a lower alkoxy group, a chlorine atom or a bromine atom.

The protective group of the hydroxy group in the formula includes usual ether-forming groups such as benzyl, allyl, benzyloxymethyl, and a lower alkoxymethyl group. The lower alkoxymethyl group herein is an alkoxymethyl group having 1 to 5 carbon atoms and examples thereof include a methoxymethyl group, a tert-butoxymethyl group, and a methoxyethoxymethyl group. The lower alkoxy group used for $R^3$ and $R^4$ is an alkoxy group having 1 to 5 carbon atoms and examples thereof include a methoxy group, an ethoxy group, an iso-propoxy group, a tert-butoxy group, and a pentyloxy group.

The compound represented by the above general formula (3) is a production intermediate for the compound represented by the general formula (2).

Furthermore, racemic body, meso form, and optically active isomers of the compounds of the invention are also included in the invention.

The following will describe the process for producing these compounds.

Hereinafter, in order to avoid complication, the process for producing the compound of the invention is specifically illustrated using a compound (8) (hereinafter sometimes referred to as (−)-DANP) which is (−)-isomer of optically active isomers of the compound represented by the following formula (7) (hereinafter sometimes referred to as DANP) as an example, among the compounds of the invention. However, the process of the invention is not limited to the example.

(7)

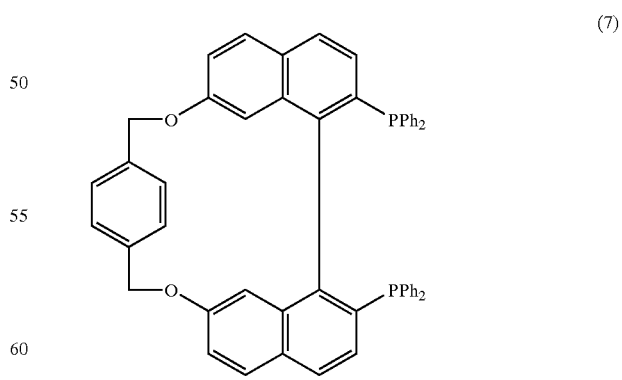

wherein Ph is a phenyl group.

For example, the above compound is synthesized according to the following process.

That is, 7-benzyloxy-naphthalen-2-ol (9) is dimerized in the presence of copper chloride and t-butylamine to form a compound (10), which is subjected to optical resolution using quinine to obtain an optically active isomer (R)-(−)-(10). The optically active isomer (R)-(−)-(10) is reacted with chloromethyl methyl ether (MOMCl) in the presence of diisopropylethylamine to form a compound (11), which is debenzylated in the presence of 5% palladium-carbon and ammonium formate to obtain a compound (12). Then, the compound (12) is reacted with p-xylylene dibromide in the presence of cesium carbonate to form a compound (13) and successively, the compound (13) is deprotected by adding hydrochloric acid to obtain a compound (14). The aimed compound (−)-DANP (8) can be produced by reacting the compound (14) with trifluoromethanesulfonic anhydride in the presence of pyridine to form a compound (15) and then reacting the compound (15) with diphenylphosphine in the presence of a palladium catalyst.

The process is shown in Scheme 1.

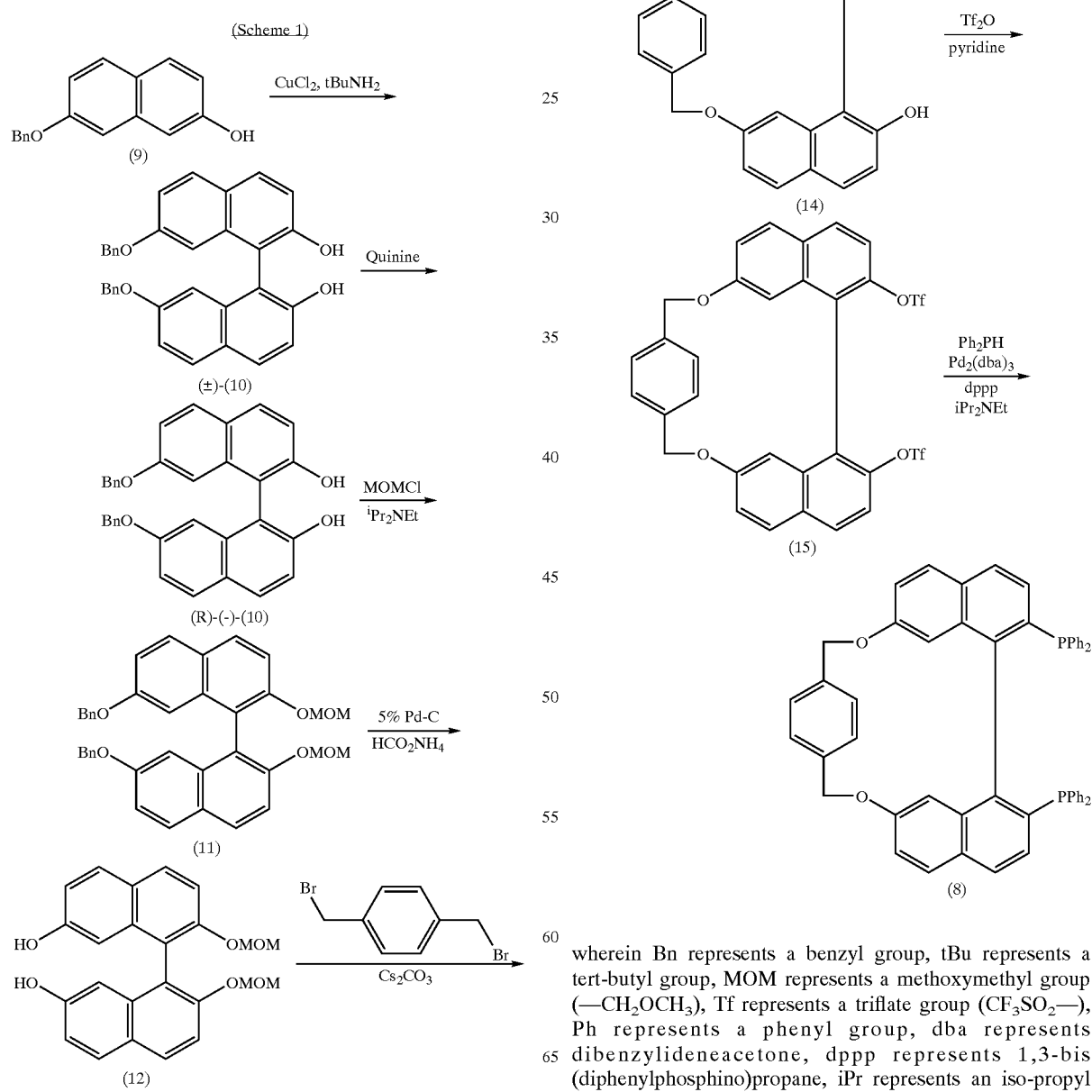

wherein Bn represents a benzyl group, tBu represents a tert-butyl group, MOM represents a methoxymethyl group (—CH$_2$OCH$_3$), Tf represents a triflate group (CF$_3$SO$_2$—), Ph represents a phenyl group, dba represents dibenzylideneacetone, dppp represents 1,3-bis(diphenylphosphino)propane, iPr represents an iso-propyl group, and Et represents an ethyl group.

Moreover, (+)-isomer (referred to as (+)-DANP) of the optically active isomers of the compound represented by the above formula (7) is obtained by carrying out optical resolution of the compound (10) in the above Scheme 1 in the presence of quinidine to obtain (+)-isomer of the compound and then carrying out similar operations.

Furthermore, the compound which is a diphosphine compound described in claim 1 and wherein $R^1$ and $R^2$ are substituted phenyl groups can be produced utilizing a diphenylphosphine derivative having corresponding substituents instead of diphenylphosphine in the process shown in the above Scheme 1.

In addition, the compound which is a diphosphine compound described in claim 1 and wherein $R^1$ and $R^2$ are groups other than phenyl groups or substituted phenyl groups can be also produced in a similar manner to the process shown in the above Scheme 1, utilizing a corresponding phosphine derivative instead of diphenylphosphine.

Of the compounds of the invention, the compound (1), in particular an optically active compound thereof is useful as a ligand for a transition metal complex. Moreover, the compound (2) is useful as a production intermediate of the compound (1). Furthermore, the compound (3) is useful as a production intermediate of the compound (2).

The following will describe the transition metal complex.

As preferred transition metal complexes, the following compounds can be mentioned.

A transition metal complex represented by the general formula (4):

$$M_m L_n X_p Q_q \quad (4)$$

wherein M is a transition metal selected from rhodium, ruthenium, iridium, palladium, and nickel and L represents an optically active diphosphine compound of the compound according to claim 1; X is selected from the group consisting of Cl, Br, I, an acetoxy group, a methallyl group, and a π-allyl group; and Q is selected from the group consisting of $NEt_3$ (wherein Et represents an ethyl group) and an dialkylammonium ion, the alkyl group of the dialkylammonium ion being an alkyl group having 1 to 5 carbon atoms, provided that when M=Rh, X=Cl, Br, or I and m=2, n=2, p=2, and q=0, when M=Ru and X=an acetoxy group, m=1, n=1, p=2 and q=0, when M=Ru and X=a methallyl group, m=1, n=1, p=2 and q=0, when M=Ru, X=Cl, Br, or I, and Q=$NEt_3$, m=2, n=2, p=4, and q=1, when M=Ru, X=Cl, Br, or I, and Q=an dialkylammonium ion, m=n=2, p=5, and q=1, when M=Ir, X=Cl, Br, or I and m=2, n=2, p=2, and q=0, when M=Pd and X=Cl, Br, or I, m=1, n=1, p=2, and q=0, when M=Pd and X=a π-allyl group, m=2, n=2, p=2, and q=0, and when M=Ni, X=Cl, Br, or I and m=1, n=1, p=2, and q=0.

A transition metal complex represented by the general formula (5):

$$[M_m L_n X_p Z_q] Y_r \quad (5)$$

wherein M is a transition metal selected from rhodium, ruthenium, iridium, palladium, and nickel and L represents an optically active diphosphine compound of the compound according to claim 1; X is selected from the group consisting of 1,5-cyclooctadiene (hereinafter referred to as cod), norbornadiene (hereinafter referred to as nbd), a π-allyl group, Cl, Br, and I; Z represents benzene or p-cymene; and Y is selected from the group consisting of $BF_4$, $ClO_4$, $PF_6$, $BPh_4$, Cl, Br, and I (Ph represents a phenyl group), provided that when M=Rh, X=cod or nbd, Y=$BF_4$, $ClO_4$, $PF_6$, or $BPh_4$, and m=1, n=1, p=1, q=0, and r=1, when M=Ru and Y=Cl, Br, or I, X=Cl, Br, or I, Z=benzene or p-cymene, and m=1, n=1, p=1, q=1, and r=1, when M=Ru and Y=$BF_4$, $ClO_4$, $PF_6$, or $BPh_4$, m=1, n=1, p=0, q=0, and r=2, when M=Ir, X=cod or nbd, Y=$BF_4$, $ClO_4$, $PF_6$, or $BPh_4$, and m=1, n=1, p=1, q=0, and r=1, when M=Pd and p=0, Y=$BF_4$, $ClO_4$, $PF_6$, or $BPh_4$ and m=1, n=1, q=0, and r=1, when M=Pd and X=a π-allyl group, Y=Cl, Br, I, $BF_4$, $ClO_4$, $PF_6$, or $BPh_4$ and m=1, n=1, p=1, q=0, and r=1, and when M=Ni, X=Cl, Br, or I and m=1, n=1, p=2, q=0, and r=0.

A transition metal which forms the complex in the invention includes rhodium, ruthenium, iridium, palladium, nickel, and the like.

These transition metal complexes can be produced using a known method.

In this connection, with regard to the symbols used in the formulae shown in the following transition metal complexes, L represents an optically active compound among the compounds (1) of the invention, cod represents 1,5-cyclooctadiene, nbd represents norbornadiene, Ph represents a phenyl group, and Ac represents an acetyl group.

The following will illustrate the complexes specifically.

Rhodium Complexes:

As a specific example of producing the rhodium complex, there may be mentioned a synthetic method wherein bis (cycloocta-1,5-diene) rhodium(I) tetrafluoroborate salt is reacted with a diphosphine compound of the invention DANP according to the method described in the Chemical Society of Japan ed., 4th edition Jikken Kagaku Koza (Lecture of Experimental Chemistry), vol. 18, Yuki Kinzoku Sakutai (Organic Metal Complexes), 1991, Maruzen, pp. 339–344. The following can be mentioned as specific examples of the rhodium complexes.

$[Rh(L)Cl]_2$, $[Rh(L)Br]_2$, $[Rh(L)I]_2$,
$[Rh(cod) (L) ]BF_4$, $[Rh (cod) (L) ]ClO_4$, $[Rh (cod) (L)]PF_6$,
$[Rh(cod)(L)]BPh_4$, $[Rh(nbd)(L)]BF_4$, $[Rh(nbd)(L)]ClO_4$,
$[Rh(nbd)(L)]PF_6$, $[Rh(nbd)(L)]BPh_4$ Ruthenium Complexes:

As the method for producing the ruthenium complex, there may be mentioned a preparative method wherein $[Ru(cod)Cl_2]_n$ and a diphosphine compound of the invention DANP are heated under reflux in toluene solvent in the presence of triethylamine as described in a literature (T. Ikariya, Y. Ishii, H. Kawano, T. Arai, M. Saburi, S. Yoshikawa, and S. Akutagawa, J. Chem. Soc., Chem. Commun., 922 (1985)). Moreover, there may be also mentioned a preparative method wherein $[Ru(p-cymene)I_2]_2$ and DANP are heated under stirring in methylene chloride and ethanol according to the method described in a literature (K. Mashima, K. Kusano, T. Ohta, R. Noyori, H. Takaya, J. Chem. Soc., Chem. Commun., 1208 (1989)). The following can be mentioned as specific examples of the ruthenium complexes.

RU(OAC)$_2$(L),
Ru$_2$Cl$_4$(L)$_2$NEt$_3$, Ru$_2$Br$_4$(L)$_2$NEt$_3$,
Ru (methallyl)$_2$ (L),
[{RuCl(L)}$_2$ ($\mu$-Cl)$_3$][Me$_2$NH$_2$], [{RuCl(L)}$_2$($\mu$-Cl)$_3$] [Et$_2$NH$_2$],
[RuCl(benzene)(L)]Cl, [RuBr(benzene)(L)]Br,
[RuI(benzene)(L)]I,
[RuCl(p-cymene)(L)]Cl, [RuBr(p-cymene)(L)]Br, [RuI(p-cymene) (L)]I,
[Ru(L)](BF$_4$)$_2$, [Ru(L)](ClO$_4$)$_2$, [Ru(L)](PF$_6$)$_2$, [Ru(L)] (BPh$_4$)$_2$ Iridium Complexes:

The iridium complex can be prepared by reacting a diphosphine compound of the invention DANP with [Ir(cod) (CH$_3$CN)$_2$]BF$_4$ in tetrahydrofuran according to the method described in a literature (K. Mashima, T. Akutagawa, X. Zhang, T. Taketomi, H. Kumobayashi, S. Akutagawa, J. Organomet. Chem., 1992, 428, 213). The following can be mentioned as specific examples of the iridium complexes.

[Ir(L)Cl]$_2$, [Ir(L)Br]$_2$, [Ir(L)I]$_2$,
[Ir(cod)(L)]BF$_4$, [Ir(cod)(L)]ClO$_4$, [Ir(cod)(L)]PF$_6$,
[Ir (cod) (L) ]BPh$_4$,
[Ir(nbd)(L)]BF$_4$, [Ir(nbd)(L)]ClO$_4$, [Ir(nbd)(L)]PF$_6$,
[Ir(nbd) (L)]BPh$_4$ Palladium Complexes:

The palladium complex can be prepared by reacting a diphosphine compound of the invention DANP with $\pi$-allylpalladium chloride according to the method described in a literature (Y. Uozumi and T. Hayashi, J. Am. Chem. Soc., 1991, 113, 9887). The following can be mentioned as specific examples of the palladium complexes.

PdCl$_2$(L), PdBr$_2$(L), PdI$_2$(L),
[($\pi$-allyl)Pd(L)]$_2$,
[Pd(L)]BF$_4$, [Pd(L)]ClO$_4$, [Pd(L)]PF$_6$, [Pd(L)]BPh$_4$,
[($\pi$-allyl)Pd(L)]Cl, [($\pi$-allyl)Pd(L)]BF$_4$, [($\pi$-allyl)Pd(L)] ClO$_4$, [($\pi$-allyl)Pd(L)]PF$_4$, [($\pi$-allyl)Pd(L)]BPh$_4$ Nickel Complexes:

The nickel complex can be prepared by dissolving a diphosphine compound of the invention DANP and nickel chloride in a mixed solvent of 2-propanol and methanol and heating them under stirring according to the method described in the Chemical Society of Japan ed., 4th edition Jikken Kagaku Koza (Lecture of Experimental Chemistry), vol. 18, Yuki Kinzoku Sakutai (Organic Metal Complexes), 1991, Maruzen, p. 376. The following can be mentioned as specific examples of the nickel complexes.

NiCl$_2$ (L), NiBr$_2$ (L), NiI$_2$ (L)

The transition metal complex containing the thus obtained novel optically active diphosphine compound as a ligand is useful as a catalyst for asymmetric hydrogenation. In the case of using the complex of the invention as the catalyst, the complex may be used after increasing its purity or the complex may be used without purification.

Among the above transition metal complexes, complexes containing ruthenium and an optically active diphosphine compound DANP as a ligand can achieve a higher enantioselectivity as compared with ruthenium complexes of BINAP, p-TolBINAP, or the like in the asymmetric hydrogenation of dehydronaproxen.

In the case of asymmetric hydrogenation using the above transition metal complex, substrates for the asymmetric hydrogenation include carbonyl compounds, imines, olefins, and the like, specifically, $\alpha$-ketoesters, $\beta$-ketoesters, $\gamma$-ketoesters, $\alpha$-hydroxyketones, $\beta$-hydroxyketones, enamides, enol esters, allylalcohols, and $\alpha,\beta$-unsaturated carboxylic acids, and more specifically, $\alpha,\beta$-unsaturated carboxylic acids, preferably dehydronaproxen.

The following will describe reaction conditions in the asymmetric hydrogenation using the transition metal complex of the invention. These conditions may vary depending on a substrate and a complex to be used, but the reaction is generally carried out at a temperature of 10 to 80° C. under a hydrogen pressure of 10 to 60 atm for 5 to 24 hours. The amount of the above complex to be used relative to the above substrate ranges from about 1/500 to 1/5000 (molar ratio). The reaction solvent to be used may be any one as far as it is stable and does not affect the substrate and product. Specifically, lower alcohols such as methanol and ethanol, ethers such as tetrahydrofuran, halogenated hydrocarbons such as methylene chloride and chlorobenzene are used. The amount thereof to be used may vary depending on the solubility of the substrate, but the solvent is used in an amount of about 0.1 to 100 volume equivalents (ml/g) relative to the weight of the substrate.

The novel diphosphine compound of the invention is particularly useful as a ligand for a transition metal complex. Moreover, the transition metal complex is useful as a catalyst for asymmetric hydrogenation. By using the catalyst, an asymmetric hydrogenation product having a high optical purity can be obtained in good yields, and thus the catalyst is industrially extremely useful.

The following will explain the invention in detail with reference to Examples, but the invention is by no means limited thereto.

The instruments employed for measuring physical properties in each Example are as follows.

| | |
|---|---|
| $^1$H NMR | DRX500 mfd. by Bruker (500 MHz) |
| $^{31}$P NMR | DRX500 mfd. by Bruker (202 MHz) |
| Melting point | MP-500D mfd. by Yanaco |
| Optical rotation | DIP-4 mfd. by Nihon Bunko |
| Gas chromatography | 5890-II mfd. by Hewlett Packard |
| High performance liquid chromatography | HP1100 mfd. by Hewlett Packard |
| Mass spectrometry | M-80B mfd. by Hitachi Ltd. |

EXAMPLE 1

Synthesis of Compound (13)

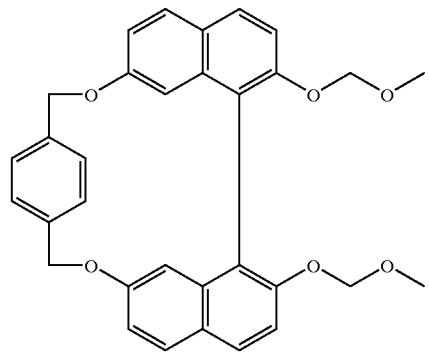

(13)

(a) Synthesis of ($\pm$)-7,7'-bis-benzyloxy-[1,1']-binaphthalene-2,2'-diol (($\pm$)-(10))

To a mixture of 55.8 g (0.223 mol) of 7-benzyloxy-naphthalene-2-ol, 60.0 g (0.446 mol) of copper chloride (II), and 1.5 L of methanol was added a methanol (500 mL)

solution of 130.5 g (1.78 mol) of t-butylamine, followed by 20 hours of stirring at room temperature. The reaction liquid was cooled on an ice bath and after addition of 500 mL of 6N hydrochloric acid, methanol was removed by evaporation under reduced pressure. The residue was dissolved in ethyl acetate (1.5 L) and the resulting solution was washed with saturated brine. The solvent was removed by evaporation under reduced pressure and the residue was purified by silica gel column chromatography to obtain 47.3 g of the title compound. Yield 85%.

EI-MS m/z 498 (M$^+$)
$^1$H-NMR (CDCl$_3$): δ4.69 (2H, d, J=11.6 Hz), 4.83 (2H, d, J=11.6 Hz), 4.99 (2H, s), 6.48 (2H, d, J=2.4 Hz), 7.07–7.25 (14H, m), 7.80 (2H, d, J=9.0 Hz), 7.89 (2H, d, J=9.0 Hz)

(b) Optical Resolution of (±)-7,7'-bis-benzyloxy-[1,1']-binaphthalene-2,2'-diol ((±)-(10))

A mixture of 43.06 g (0.086 mol) of (±)-7,7'-bis-benzyloxy-[1,1']-binaphthalene-2,2'-diol ((±)-(10)) obtained in (a), 30.81 g (0.120 mol) of quinine, and 1 L of ethanol was heated under reflux, followed by 30 minutes of stirring. The resulting solids were collected by filtration and dissolved in dichloromethane. The organic layer was washed with 1N hydrochloric acid and water, and dried over anhydrous sodium sulfate. The solvent was removed by evaporation under reduced pressure to obtain 17.76 g (99.5% ee) of (R)-(−)-7,7'-bis-benzyloxy-[1,1']-binaphthalene-2,2'-diol ((R)-(−)-(10)).

$[\alpha]_D^{24}$ −232.00 (c=1.00, CHCl$_3$)
mp: 66–68° C.

(c) Synthesis of (R)-(−)-7,7'-bis-benzyloxy-2,2'-bis-methoxymethoxy[1,1']-binaphthalene (11)

Under a nitrogen stream, a mixture of 42.42 g (0.085 mol) of (R)-(−)-7,7'-bis-benzyloxy-[1,1]-binaphthalene-2,2'-diol ((R)-(−)-(10)) obtained in (b), 45 mL (0.258 mol) of diisopropylethylamine, and 420 mL of dichloromethane was cooled to 4° C. and 45 mL (0.258 mol) of chloromethyl methyl ether was added thereto, followed by stirring at room temperature overnight. The reaction liquid was washed with 1N hydrochloric acid and water, successively, and dried over anhydrous sodium sulfate, and then the solvent was removed by evaporation under reduced pressure. The residue was filtered through silica gel to obtain 49.5 g of the title compound. Yield 99%.

$[\alpha]_D^{24}$ −101.4° (c=0.50, CHCl$_3$)
EI-MS m/z 586 (M$^+$)
$^1$H-NMR (CDCl$_3$): δ3.13 (6H, s), 4.70 (4H, s), 4.89 (2H, d, J=6.6 Hz), 4.97 (2H, d, J=6.6 Hz), 6.47 (2H, d, J=2.4 Hz), 7.10–7.21 (10H, m), 7.40 (2H, d, J=9.0 Hz), 7.78 (2H, d, J=9.0 Hz), 7.86 (2H, d, J=9.0 Hz)

(d) Synthesis of (R)-(−)-2,2'-bis-methoxymethoxy[1,1']-binaphthalene-7,7'-diol (12)

A mixture of 45.0 g (0.076 mol) of (R)-(−)-7,7'-bis-benzyloxy-2,2'-bis-methoxymethoxy[1,1']-binaphthalene (11) obtained in (c), 45 g of 5% palladium-carbon, 115 g (1.82 mol) of ammonium formate, and 800 mL of methanol was heated under reflux for 6 hours. The reaction liquid was filtered through celite and the filtrate was concentrated. The residue was dissolved in ethyl acetate and the resulting solution was washed with water and saturated brine, successively. After drying over anhydrous sodium sulfate, the solution was filtered through silica gel and the solvent was evaporated to obtain 30.2 g of the title compound. Yield 98%.

$[\alpha]_D^{24}$ −43.8° (c=0.50, CH$_3$OH)
mp: 189–190° C.
EI-MS m/z 406 (M$^+$)
$^1$H-NMR (CDCl$_3$): δ3.20 (6H, s), 5.01 (2H, d, J=6.8 Hz), 5.12 (2H, d, J=6.8 Hz), 6.47 (2H, d, J=2.4 Hz), 6.95 (2H, dd, J=8.8, 2.4 Hz), 7.40 (2H, d, J=9.0 Hz), 7.77 (2H, d, J=8.8 Hz), 7.86 (2H, d, J=8.8 Hz)

(e) Synthesis of Compound (13)

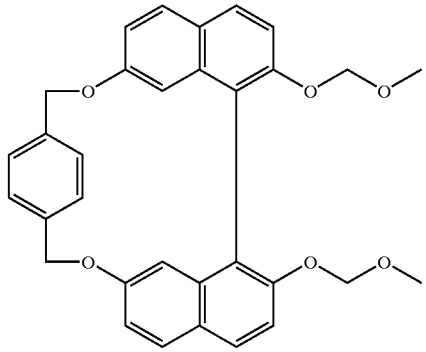

(13)

Under a nitrogen stream, a mixture of 29.75 g (73.2 mmol) of (R)-(−)-2,2'-bis-methoxymethoxy[1,1']-binaphthalene-7,7'-diol (12) obtained in (d), 37.43 g (115 mmol) of cesium carbonate, and 750 mL of N,N-dimethylformamide was heated under reflux at 60° C. and an N,N-dimethylformamide (750 mL) solution of 20.50 g (77.7 mmol) of p-xylylene dibromide was added dropwise thereto, followed by stirring at the same temperature overnight. The reaction liquid was filtered and the solvent was removed by evaporation under reduced pressure. The residue was dissolved in chloroform, the resulting solution was washed with water, and then the solvent was removed by evaporation under reduced pressure. To the residue was added 120 mL of ethyl acetate, followed by 1 hour of heating under reflux. The resulting solids were collected by filtration to obtain 29.33 g of the title compound.
Yield 78.6%.

$[\alpha]_D^{24}$ −352.0° (c=0.50, CHCl$_3$)
mp: 220–221.5° C.
EI-MS m/z 508 (M$^+$)
$^1$H-NMR (CDCl$_3$): δ3.05 (6H, s), 4.84 (2H, d, J=6.6 Hz), 4.87 (2H, d, J=11.6 Hz), 4.95 (2H, d, J=6.6 Hz), 5.06 (2H, d, J=11.6 Hz), 5.86 (2H, d, J=2.2 Hz), 6.48 (2H, dd, J=7.8, 1.6 Hz), 6.97 (2H, dd, J=7.6, 1.6 Hz), 7.25 (2H, dd, J=8.8, 2.4 Hz), 7.38 (2H, d, J=9.0 Hz), 7.83 (4H, d, J=8.8 Hz)

EXAMPLE 2

Synthesis of Compound (14)

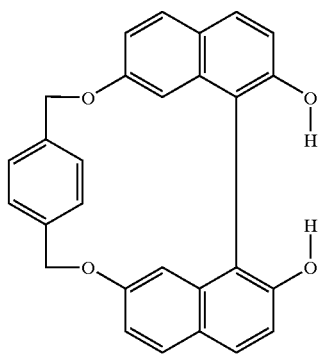

(14)

A mixture of 28.8 g (56.6 mmol) of the compound (13) obtained in (e) of Example 1, 2 L of tetrahydrofuran, and 30 mL of 35% hydrochloric acid was heated under reflux for 2 hours. The reaction liquid was concentrated and then the residue was purified by silica gel column chromatography to obtain 22.02 g of the title compound.
Yield 92.6%.
$[\alpha]_D^{28}$ −455.1° (c=0.50, CHCl$_3$)
mp: 96–97° C.
EI-MS m/z 420 (M$^+$)
$^1$H-NMR (CDCl$_3$): δ4.89 (2H, d, J=11.6 Hz), 5.09 (2H, d, J=11.6 Hz), 5.79 (2H, d, J=2.2 Hz), 6.49 (2H, dd, J=8.2, 1.4 Hz), 6.98 (2H, dd, J=8.0, 1.4 Hz), 7.20 (2H, d, J=8.8 Hz), 7.24–7.29 (4H, m), 7.83 (2H, d, J=2.6 Hz), 7.87 (2H, d, J=2.6 Hz)

EXAMPLE 3

Synthesis of Compound (15)

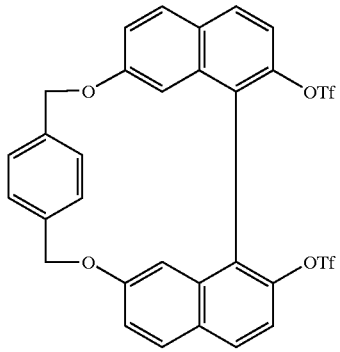

(15)

Under a nitrogen stream, a mixture of 1.12 g (2.66 mmol) of the compound (14) obtained in Example 2, 12 mL of dichloromethane, and 1.1 mL (13.6 mmol) of pyridine was cooled on an ice bath and 1.1 mL (6.52 mmol) of trifluoromethanesulfonic anhydride was added thereto, followed by 87 hours of stirring at room temperature. The reaction liquid was diluted with dichloromethane and washed with 1N hydrochloric acid and water, successively. The organic layer was dried over anhydrous sodium sulfate, and then the solvent was removed by evaporation under reduced pressure. The residue was purified by silica gel column chromatography to obtain 1.48 g of the title compound.
Yield 81.2%.
$[\alpha]_D^{24}$ −318.9° (c=0.50, CHCl$_3$)
mp: 86–88° C.
EI-MS m/z 684 (M$^+$)
$^1$H-NMR (CDCl$_3$): δ4.96 (2H, d, J=11.9 Hz), 5.12 (2H, d, J=11.9 Hz), 5.95 (2H, d, J=2.1 Hz), 6.55 (2H, dd, J=7.8, 1.6 Hz), 7.01 (2H, dd, J=7.8, 1.6 Hz), 7.42 (2H, d, J=9.0 Hz), 7.48 (2H, dd, J=9.0, 2.2 Hz), 7.95 (2H, d, J=9.0 Hz), 8.01 (2H, d, J=9.0 Hz)

EXAMPLE 4

Synthesis of Compound (8) ((−)-DANP)

Under a nitrogen stream, a mixture of 4.00 g (5.84 mmol) of the compound (15) obtained in Example 3, 317.0 mg (0.31 mmol) of Pd$_2$(dba)$_3$.CHCl$_3$, 271.2 mg (0.66 mmol) of 1,3-bisdiphenylphosphinopropne, 40 mL of N,N-dimethylformamide, and 3.0 mL (17.2 mmol) of diisopropylethylamine was heated at 100° C. under stirring and during the heating under stirring, 2.6 mL (1.5 mmol) of diphenylphosphine was added thereto, followed by 3 days of stirring at the same temperature. The reaction liquid was diluted with dichloromethane and washed with 1N hydrochloric acid and water, successively. The organic layer was dried over anhydrous magnesium sulfate, and then the solvent was removed by evaporation under reduced pressure. The residue was filtered through silica gel and then reprecipitated from methanol to obtain 2.35 g of the title compound.
Yield 53.3%. (dba=dibenzylideneacetone)
$[\alpha]_D^{24}$ −62.70 (c=0.244, CHCl$_3$)
mp: 295° C. (decomposition)
CI-MS m/z 757 (M$^+$+1)
$^1$H-NMR (CDCl$_3$): δ4.77 (2H, d, J=11.9 Hz), 4.85 (2H, d, J=11.9 Hz), 5.43 (2H, d, J=2.3 Hz), 6.32 (2H, dd, J=7.8, 1.7 Hz), 6.79 (2H, dd, J=7.8, 1.7 Hz), 6.87 (4H, m), 7.04–7.25 (20H, m), 7.75 (4H, d, J=8.8 Hz)
$^{31}$P-NMR (CDCl$_3$): δ−12.8

EXAMPLE 5

Synthesis of Compound (16) (Hereinafter Referred to as (−)-DM-DANP)

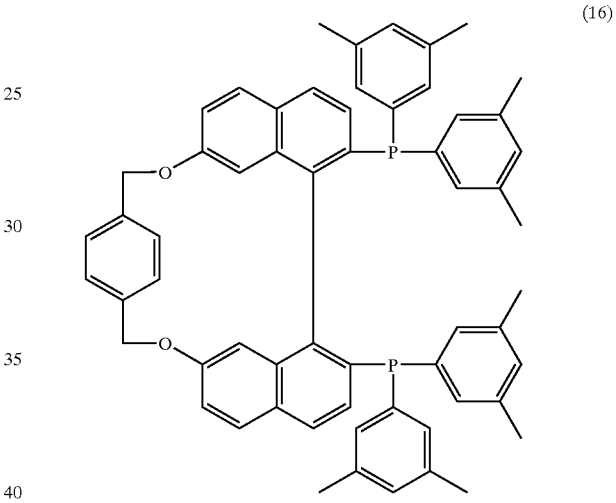

(16)

Under a nitrogen stream, a mixture of 1.10 g (1.60 mmol) of the compound (15) obtained in Example 3, 167.2 mg (0.16 mmol) of Pd$_2$(dba)$_3$.CHCl$_3$, 144.0 mg (0.35 mmol) of 1,3-bisdiphenylphosphinopropne, 10 mL of N,N-dimethylformamide, and 0.87 mL (5.0 mmol) of diisopropylethylamine was heated at 100° C. under stirring and during the heating under stirring, 1.2 g (5.0 mmol) of di(3,5-dimethylphenyl)phosphine was added thereto, followed by 84 hours of stirring at the same temperature. The reaction liquid was diluted with dichloromethane and washed with 1N hydrochloric acid and water, successively. The organic layer was dried over anhydrous magnesium sulfate, and then the solvent was removed by evaporation under reduced pressure. The residue was purified by silica gel column chromatography to obtain 0.65 g of the title compound.
Yield 46.8%. (dba=dibenzylideneacetone)
$[\alpha]_D^{24}$ −39.60 (c=0.50, CHCl$_3$)
mp: 140–142° C.
CI-MS m/z 869 (M$^+$+1)
$^1$H-NMR (CDCl$_3$): δ2.03 (12H, s), 2.12 (12H, s), 4.79 (2H, d, J=11.9 Hz), 4.88 (2H, d, J=11.9 Hz), 5.57 (2H, d, J=2.2 Hz), 6.33 (2H, dd, J=7.7, 1.8 Hz), 6.55 (2H, d, J=6.5 Hz), 6.71–6.78 (10H, m), 7.28 (2H, dd, J=8.8, 2.3 Hz), 7.35 (2H, dd, J=8.4, 2.6 Hz), 7.74 (2H, d, J=8.3 Hz), 7.79 (2H, d, J=8.8 Hz)
$^{31}$P-NMR (CDCl$_3$): δ−12.5

EXAMPLE 6

Preparation of [RuCl(p-cymene)((−)-DANP)]Cl

A mixture of 30.8 mg (0.05 mmol) of [Ru(p-cymene)Cl$_2$]$_2$, 76.2 mg (0.10 mmol) of (−)-DANP obtained in Example 4, 4 mL of methylene chloride, and 4 mL of ethanol was stirred at 50° C. for 3 hours in a 20 mL Schlenk tube. The solvent was removed by evaporation under reduced pressure and then the residue was dried under vacuum to obtain 107.0 mg of the title compound.

$^{31}$P-NMR (CD$_2$Cl$_2$): δ42.9 (d, J=62.8 Hz), 27.1 (d, J=62.8 Hz)

EXAMPLE 7

Preparation of [Ru(OAc)$_2$((−)-DANP)] (Wherein Ac Represents an Acetyl Group)

Under a nitrogen stream, a mixture of 106.2 mg (0.10 mmol) of [RuCl(p-cymene)((−)-DANP)]Cl obtained in Example 6, 164.2 mg (2.0 mmol) of sodium acetate, and 5 mL of 1,4-dioxane was heated under reflux for 16 hours in a 20 mL Schlenk tube. After filtration through celite, the solvent was removed by evaporation under reduced pressure to obtain 97.0 mg of the title compound.

$^{31}$P-NMR (CD$_2$Cl$_2$): δ64.9 (s)

EXAMPLE 8

Preparation of [RuCl(p-cymene)((−)-DM-DANP)]Cl

A mixture of 70.5 mg (0.115 mmol) of [Ru(p-cymene)Cl$_2$]$_2$, 200.5 mg (0.230 mmol) of (−)-DM-DANP obtained in Example 5, 4 mL of methylene chloride, and 4 mL of ethanol was stirred at 50° C. for 3 hours in a 20 mL Schlenk tube. The solvent was removed by evaporation under reduced pressure and then the residue was dried under vacuum to obtain 271.0 mg of the title compound.

$^{31}$P-NMR (CD$_2$Cl$_2$): δ40.7 (d, J=61.7 Hz), 29.8 (d, J=61.7 Hz)

EXAMPLE 9

Preparation of [Ru(OAc)$_2$ ((−)-DM-DANP)] (Wherein Ac Represents an Acetyl Group)

Under a nitrogen stream, 117.1 mg (0.10 mmol) of [RuCl(p-cymene)((−)-DM-DANP)]Cl obtained in Example 8, 164.2 mg (2.0 mmol) of sodium acetate, and 5 mL of 1,4-dioxane were charged into a 20 mL Schlenk tube, and the whole was heated under reflux for 16 hours. After filtration through celite, the solvent was removed by evaporation under reduced pressure to obtain 109.0 mg of the title compound.

$^{31}$P-NMR (CD$_2$Cl$_2$): δ64.9 (s)

Use Example 1 Asymmetric Hydrogenation of Dehydronaproxen

Into a stainless steel autoclave were charged 2.1 mg (0.0022 mmol) of the complex obtained in Example 7, 0.5 g (2.2 mmol) of dehydronaproxen, and 3 mL of methanol, and the whole was heated under stirring at 15° C. under a hydrogen pressure of 50 atm for 19 hours to obtain optically active naproxen. When conversion and optical purity of the resulting optically active naproxen were measured on a high performance liquid chromatography, the conversion was 96.8% or more and the optical purity was 85.7% ee.

The conversion and optical purity were measured under the following conditions.

SUMICHIRAL OA-2500 (4.6 mm×250 mm)

Eluent: 0.05 M ammonium acetate methanol solution

Flow: 1.0 mL/min.

Detect: 254 nm

Use Example 2 Asymmetric Hydrogenation of Dehydronaproxen

Into a stainless steel autoclave were charged 4.8 mg (0.0044 mmol) of the complex obtained in Example 9, 0.5 g (2.2 mmol) of dehydronaproxen, and 3 mL of methanol, and the whole was heated under stirring at 15° C. under a hydrogen pressure of 50 atm for 7 hours to obtain optically active naproxen. When conversion and optical purity of the resulting optically active naproxen were measured on a high performance liquid chromatography, the conversion was 99% or more and the optical purity was 92.3% ee. In this connection, the conversion and optical purity were measured in a similar manner to Use Example 1.

Comparative Example 1

Asymmetric hydrogenation was carried out in a similar manner to Use Example 1 with the exception that the ruthenium complex was replaced by Ru$_2$Cl$_4$[(R)-p-Tolbinap]$_2$NEt$_3$, whereby optically active naproxen was obtained. The conversion was 93.1% and the optical purity was 87.0% ee.

While the invention has been described in detail and with reference to specific embodiments thereof, it will be apparent to one skilled in the art that various changes and modifications can be made therein without departing from the scope thereof.

This application is based on Japanese patent application No. 2002-162463 filed Jun. 4, 2002, the entire contents thereof being hereby incorporated by reference.

What is claimed is:

1. A diphosphine compound represented by the general formula (1):

wherein R$^1$ and R$^2$ each independently represents a lower alkyl group, a cycloalkyl group, an unsubstituted or substituted phenyl group, or a five-membered heteroaromatic ring residue.

2. A compound represented by the general formula (2):

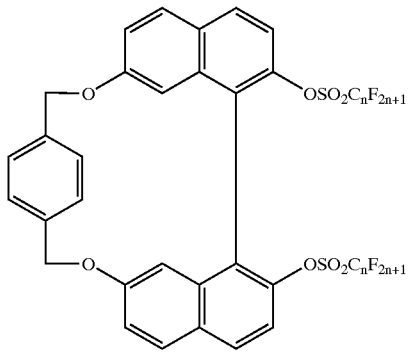

(2)

wherein n is an integer of 1 to 3.

3. A compound represented by the general formula (3):

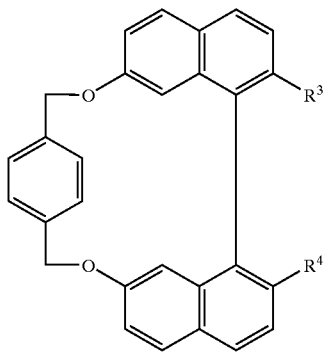

(3)

wherein $R^3$ and $R^4$ each independently represents a hydroxy group, a protected hydroxy group, a lower alkoxy group, a chlorine atom, or a bromine atom.

4. A transition metal complex containing an optically active compound of the compound according to claim 1 and a transition metal selected from the group consisting of rhodium, ruthenium, iridium, palladium, and nickel.

5. A catalyst containing a transition metal complex represented by the general formula (4):

$$M_mL_nX_pQ_q \quad (4)$$

wherein M is a transition metal selected from rhodium, ruthenium, iridium, palladium, and nickel and L represents an optically active diphosphine compound of the compound according to claim 1; X is selected from the group consisting of Cl, Br, I, an acetoxy group, a methallyl group, and a π-allyl group; and Q is selected from the group consisting of NEt$_3$ (wherein Et represents an ethyl group) and an dialkylammonium ion, provided that when M=Rh, X=Cl, Br, or I and m=2, n=2, p=2, and q=0, when M=Ru and X=an acetoxy group, m=1, n=1, p=2 and q=0, when M=Ru and X=a methallyl group, m=1, n=1, p=2 and q=0, when M=Ru, X=Cl, Br, or I, and Q=NEt$_3$, m=2, n=2, p=4, and q=1, when M=Ru, X=Cl, Br, or I, and Q=an dialkylammonium ion, m=n=2, p=5, and q=1, when M=Ir, X=Cl, Br, or I and m=2, n=2, p=2, and q=0, when M=Pd and X=Cl, Br, or I, m=1, n=1, p=2, and q=0, when M=Pd and X=a π-allyl group, m=2, n=2, p=2, and q=0, and when M=Ni, X=Cl, Br, or I and m=1, n=1, p=2, and q=0.

6. A catalyst containing a transition metal complex represented by the general formula (5):

$$[M_mL_nX_pZ_q]Y_r \quad (5)$$

wherein M is a transition metal selected from rhodium, ruthenium, iridium, palladium, and nickel and L represents an optically active diphosphine compound of the compound according to claim 1; X is selected from the group consisting of a π-allyl group, cod, nbd, Cl, Br, and I; Z represents benzene or p-cymene; and Y is selected from the group consisting of BF$_4$, ClO$_4$, PF$_6$, BPh$_4$, Cl, Br, and I, and cod represents 1,5-cyclooctadiene, nbd represents norbornadiene, and Ph represents a phenyl group, provided that when M=Rh, X=cod or nbd, Y=BF$_4$, ClO$_4$, PF$_6$, or BPh$_4$, and m=1, n=1, p=1, q=0, and r=1, when M=Ru and Y=Cl, Br, or I, X=Cl, Br, or I, Z=benzene or p-cymene, and m=1, n=1, p=1, q=1, and r=1, when M=Ru and Y=BF$_4$, ClO$_4$, PF$_6$, or BPh$_4$, m=1, n=1, p=0, q=0, and r=2, when M=Ir, X=cod or nbd, Y=BF$_4$, ClO$_4$, PF$_6$, or BPh$_4$, and m=1, n=1, p=1, q=0, and r=1, when M=Pd and X=a π-allyl group, Y=Cl, Br, I, BF$_4$, ClO$_4$, PF$_6$, or BPh$_4$ and m=1, n=1, p=1, q=0, and r=1, when M=Pd and p=0, Y=BF$_4$, ClO$_4$, PF$_6$, or BPh$_4$ and m=1, n=1, q=0, and r=1, and when M=Ni, X=Cl, Br, or I and m=1, n=1, p=2, q=0, and r=0.

7. A catalyst for asymmetric hydrogenation, which contains the transition metal complex according to claim 4.

* * * * *